(12) United States Patent
Frisch (10) Patent No.: US 7,419,594 B2
(45) Date of Patent: Sep. 2, 2008

(54) APPARATUS AND METHOD FOR CONTROLLING BIOMASS GROWTH IN SUSPENDED CARRIER BIOREACTOR

(75) Inventor: Samuel Frisch, Manalapan, NJ (US)

(73) Assignee: Shaw Environmental & Infrastructure, Inc., Lawrenceville, NJ (US)

( * ) Notice: Subject to any disclaimer, the term of this patent is extended or adjusted under 35 U.S.C. 154(b) by 129 days.

(21) Appl. No.: 11/107,946

(22) Filed: Apr. 15, 2005

(65) Prior Publication Data

US 2005/0178725 A1 Aug. 18, 2005

Related U.S. Application Data

(63) Continuation-in-part of application No. 10/682,624, filed on Oct. 9, 2003, now Pat. No. 7,018,534.

(51) Int. Cl.
C02F 3/22 (2006.01)
(52) U.S. Cl. .................. 210/608; 210/629; 210/620; 210/197; 210/220; 210/540
(58) Field of Classification Search ............ 210/608, 210/620, 629, 194, 197, 220, 540
See application file for complete search history.

(56) References Cited

U.S. PATENT DOCUMENTS

| | | | | |
|---|---|---|---|---|
| 2,024,986 A | * | 12/1935 | Durdin, Jr. ............... | 210/629 |
| 2,638,444 A | * | 5/1953 | Kappe ..................... | 210/194 |
| 3,043,433 A | * | 7/1962 | Singer ..................... | 210/629 |
| 3,152,982 A | * | 10/1964 | Pagnotti ................... | 210/629 |
| 3,182,801 A | * | 5/1965 | Griffith ................... | 210/540 |
| 3,224,964 A | * | 12/1965 | Derenk et al. ............. | 210/540 |
| 4,137,171 A | | 1/1979 | Yokata | |
| 4,452,701 A | | 6/1984 | Garrett et al. | |
| 4,454,038 A | | 6/1984 | Shimodaira et al. | |
| 4,521,311 A | | 6/1985 | Fuchs et al. | |

(Continued)

FOREIGN PATENT DOCUMENTS

JP 102 44 295 9/1998

(Continued)

OTHER PUBLICATIONS

Translation of Japanese patent 10-244295, Sep. 1998.*

(Continued)

*Primary Examiner*—Christopher Upton
(74) *Attorney, Agent, or Firm*—RatnerPrestia (57) ABSTRACT

A bioreactor configured to contain an aqueous suspension of biomass and media is provided. The invention includes a lift tube disposed within the vessel, the lift tube having an inlet disposed at the bottom region of the vessel and an outlet disposed at the top region of the vessel. Disposed at the bottom of the lift tube is a gas inlet positioned to feed gas into the lift tube at a location proximal to the inlet of the lift tube. An adjustable weir is disposed proximal to the outlet of the lift tube, the weir being adjustable between a lower position and a higher position. Biomass is removed from the weir and the weir height is adjustable to control the removal of biomass from the vessel. Also included as a part of the invention is a method for controlling the removal of biomass from a bioreactor as described.

17 Claims, 8 Drawing Sheets

U.S. PATENT DOCUMENTS

| | | | |
|---|---|---|---|
| 4,810,377 A | 3/1989 | Kato et al. | |
| 4,839,053 A | 6/1989 | Tharp | |
| 5,372,712 A | 12/1994 | Petit | |
| 5,942,116 A * | 8/1999 | Clark et al. | 210/194 |
| 6,077,424 A | 6/2000 | Katsukura et al. | |
| 6,168,717 B1 * | 1/2001 | Pressley et al. | 210/194 |
| 6,616,845 B2 | 9/2003 | Shechter et al. | |

FOREIGN PATENT DOCUMENTS

| | | |
|---|---|---|
| JP | 2000167579 A | 6/2000 |
| JP | 2002079283 A | 3/2002 |
| JP | 2003154385 A | 5/2003 |
| JP | 2003300086 | 10/2003 |
| WO | WO 2005/034613 A3 | 4/2005 |

OTHER PUBLICATIONS

Eckenfelder, "Principles of Water Quality Management", 1980, pp. 216 and 218.

Steel and McGhee, "Water Supply and Sewerage", 1979, pp. 503, 508 and 509.

Search Report for claim 19, application No. GB0607540.2, dated Dec. 14, 2006.

Search Report for claim 20, application No. GB0607540.2, dated Dec. 15, 2006.

Search Report for claim 21, application No. GB0607540.2, dated Dec. 15, 2006.

Search Report for claim 22, application No. GB0607540.2, dated Dec. 15, 2006.

Combined British Search and Examination Report corresponding to GB0607540.2 dated Jun. 30, 2006.

* cited by examiner

APPARATUS AND METHOD FOR CONTROLLING BIOMASS GROWTH IN SUSPENDED CARRIER BIOREACTOR

CROSS REFERENCE TO RELATED APPLICATIONS

This application is a continuation-in-part application of U.S. patent application Ser. No. 10/682,624, filed Oct. 9, 2003, now U.S. Pat. No. 7,018,534, which is incorporated by reference herein in its entirety.

FIELD OF THE INVENTION

The present invention relates to bioreactors, and more specifically, to the control of biomass growth on suspended media within fluidized-bed bioreactors.

BACKGROUND OF THE INVENTION

Biological reactors find increasing use in many areas of industry, including waste treatment plants. Efforts to protect the environment include advanced biological treatment of wastewater through the use of biological reactors, and in particular, fluidized-bed bioreactors. It is the activity of biologically active materials (or "biomass") within the biological reactor that degrades contaminants in the influent to effect a filtration process. As the biomass treats these contaminants through enzymatic reaction, the biomass grows through reproduction within the system. Typically this activity occurs within a treatment vessel which contains media or other substrate material or carriers on which the biomass attaches and grows as contaminants are consumed. Typical media would include plastic beads, resin beads, sand, or ion exchange resins, among other carriers.

Conventional fluidized-bed bioreactors, such as well-mixed suspended carrier reactors (SCRs), suffer from operational limitations in that the media or carriers of the fluidized bed may be subject to excessive buildup of biomass and precipitates, thereby causing compromised flow distribution, excessive media and/or biomass carryover, crusting, increased clogging of filters, and the like. If not properly limited, biomass and precipitate buildup is detrimental to system performance. Uncontrolled biomass film growth in a fluidized bed biological reactor can also result in an undesirable loss of media.

Media bed expansion can, under certain circumstances, be limited by the application of shear, but the success of such a control strategy depends upon whether excess biomass and suspended solids can be transported to the top of the fluidized bed. More specifically, it is recognized that such transportation of excess biomass and suspended solids toward the top of the bed is promoted by several dominant mechanisms. For example, media grains that are coated with thicker layers of biomass tend to have an overall particle density that is less than the average particle density within the fluidized bed. Those particles, therefore, are transported to the top of the fluidized bed by virtue of upward moving fluid flow as well as the reduced particle density. This upward movement results in some shear forces acting on biomass-covered particles which does separate some biomass from its supportive media.

One solution to this problem has been to increase the amount and size of cavities introduced into the system to increase the shear and subsequent separation of the biomass from its media. An example of a bioreactor in which such a system is operated is shown in FIG. 1.

Figure 1:
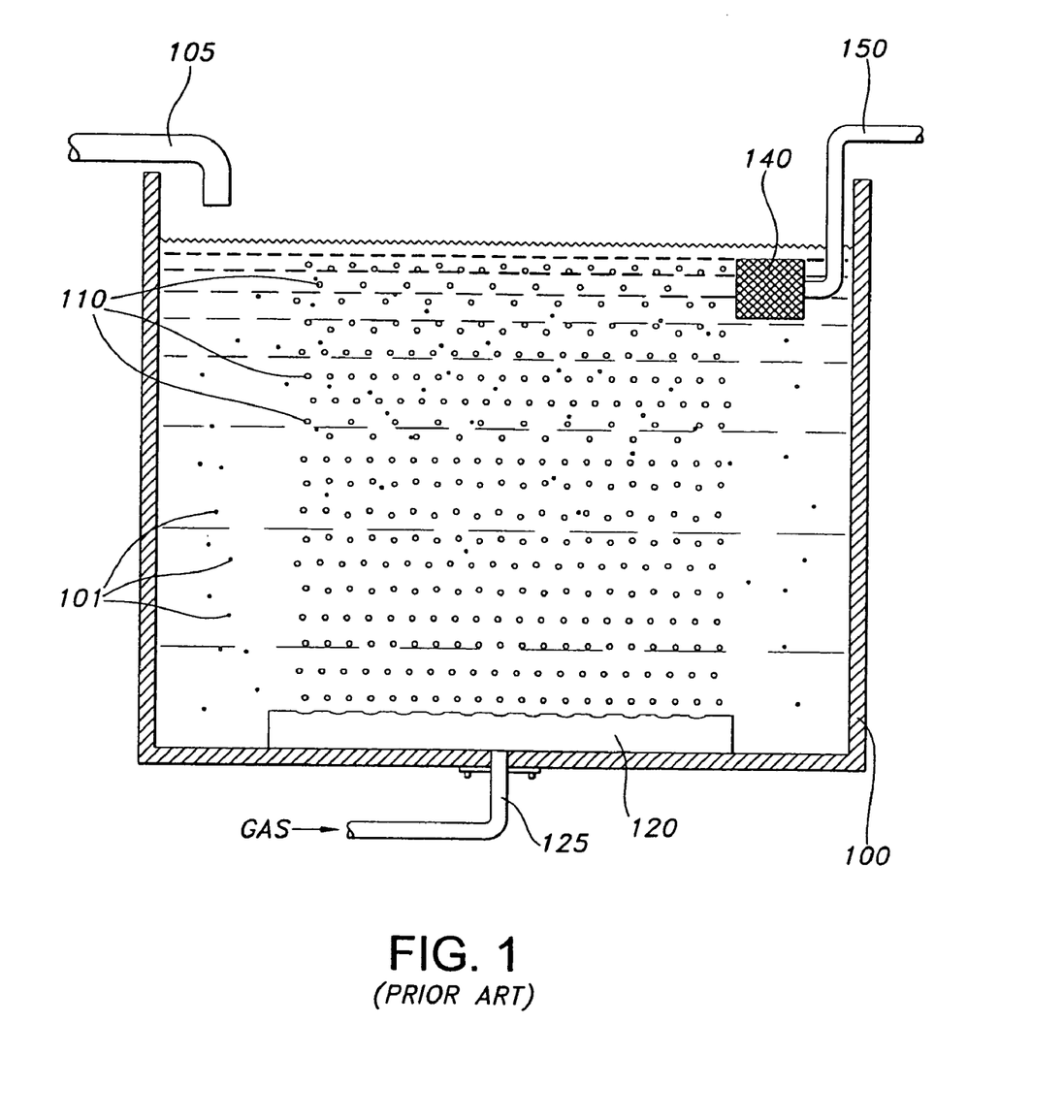
FIG. 1 schematically shows a cross-sectional view of an embodiment of a bioreactor according to the prior art.

FIG. 1 illustrates vessel 100 which contains an aqueous suspension of biomass and media, such as would be used in a waste-water treatment plant. Vessel 100 is fed by inlet pipe 105 with a waste-water stream. The biomass covered media 101 is shown as relatively small dots, and air introduced into the system is shown as cavities 110. (Some would say bubbles. For purposes of this disclosure, however, it is intended that bubble and cavity be used interchangeably). In FIG. 1, cavities 110 are shown as roughly spherical cavities of gas which travel upward through the liquid contained in vessel 100. Typically the gas is air, although it could be a gas having an oxygen enriched content (as compared to air) or even be pure oxygen. Air sparger 120 is shown at the bottom of vessel 100 and is fed air (in a typical embodiment) from line 125. Air sparger 120 in this conventional embodiment would be a coarse diffuser to create relatively large cavities and thus increase the shear forces acting on the biomass covered media. These cavities of air thus produced travel upward through the liquid in vessel 100.

The introduction of air into the liquid via air sparger (air inlet) 120 serves two purposes. First, it supplies oxygen which is needed for the enzymatic reactions which are taking place in the system as contaminants are removed and biomass is formed on the media. Secondly, the upward cavity movement causes currents to be developed in the liquid. These currents will cause movement of the media and the application of shear stresses to the media and biomass. This interaction between pieces of media with other pieces of media, fluid, biomass, and the interior wall(s) of vessel 100 results in collisions which cause: (1) contact between the microorganisms and suspended organic matter, and (2) accumulated biomass to break free from its respective supportive media. This freed biomass will typically rise to the top of the vessel as its density is less than that of the liquid system. FIG. 1 shows a filter 140 which is used to filter out the biomass as "clean" effluent water is drawn from the system through outlet pipe 150.

Many of these types of systems rely on the filtering of treated effluent (e.g. purified water in the case of waste water treatment) at filter 140 to remove clean product water or to separate the bioreactor media from the effluent. This leads to shut-down time and other expensive aspects to the operation of the reactor. As product water is drawn off and fresh waste feed is caused to flow into the reactor, it becomes necessary to remove resultant biomass. With too great a biomass concentration in the reactor, filter fouling, plugging, excessive biomass in the effluent and other problems compound to affect the reactor performance.

Thus, there remains a need in the industry for an improved system for removing accumulated biomass from a slurry of a fluidized-bed bioreactor to inhibit uncontrolled biomass growth and precipitate accumulation. Objects and advantages of the invention will become apparent to those skilled in the art from the drawings, the detailed description of preferred embodiments, and the appended claims.

SUMMARY OF THE INVENTION

The present invention provides a bioreactor comprising a vessel configured to contain an aqueous suspension of biomass and media. The invention includes a lift tube disposed within the vessel, the lift tube having an inlet disposed at the bottom region of the vessel and an outlet disposed at the top region of the vessel. A gas inlet is positioned to feed gas into the lift tube, optionally at a location proximal to the inlet of the lift tube. The gas inlet is configured to introduce a stream of gas to promote separation of the biomass from the media in the lift tube. An adjustable weir is disposed proximal to the outlet of the lift tube, the weir being adjustable between a lower position and a higher position. Means for removing biomass from the weir are provided in fluid communication with the weir, and the weir height is adjustable to control the removal of biomass from the vessel.

Also included as a part of the invention is a method for controlling the removal of biomass in a bioreactor containing a lift tube with an inlet and outlet. The method comprises the steps of introducing a stream of gas into an inlet of a lift pipe to generate sufficient shear forces to separate biomass from the media, disposing a weir proximal the outlet of the lift tube in fluid communication with a point external to the bioreactor, and adjusting the height of the weir to thereby control the removal of biomass from the bioreactor.

Another embodiment of the present invention is a bioreactor comprising a vessel configured to contain an aqueous suspension of biomass and media, a lift tube disposed within the vessel, the lift tube having an inlet disposed at the bottom region of the vessel and an outlet disposed at the top region of the vessel, a gas inlet positioned to feed gas into the lift tube, where the gas inlet is configured to introduce a stream of gas to promote separation of the biomass from the media in the lift tube, and a quiescent zone disposed proximate the lift tube inlet.

Still another embodiment is a bioreactor comprising a vessel configured to contain an aqueous suspension of biomass and media, a gas inlet at the bottom region of the vessel positioned radially outward from the geometric center of the vessel, a barrier disposed within the vessel between the gas inlet and the geometric center of the vessel, the barrier being positioned to allow the passage of the aqueous suspension of biomass and media both under and over the barrier whereby a fluid loop is formed within the vessel around the barrier when the gas inlet is introducing gas into the vessel, and a quiescent zone disposed at the bottom region of the vessel proximate the geometric center of the vessel.

Still yet another embodiment includes a bioreactor comprising a vessel configured to contain an aqueous suspension of biomass and media, a first gas inlet at the bottom region of the vessel, the first gas inlet positioned radially outward from the geometric center of the vessel, a barrier disposed within the vessel between the first gas inlet and the geometric center of the vessel, the barrier being positioned to allow passage of the aqueous suspension of biomass and media both under and over the barrier whereby a fluid flow loop is formed within the vessel around the barrier when the first gas inlet is introducing gas into the vessel, and a lift tube disposed within the vessel, the lift tube having an inlet disposed at the bottom region of the vessel and an outlet disposed at the top region of the vessel. Included in this embodiment is a second gas inlet positioned to feed gas into the lift tube, the second gas inlet being configured to introduce a second stream of gas to promote separation of the biomass from the media in the lift tube.

In yet still another embodiment, a bioreactor comprises a vessel configured to contain an aqueous suspension of biomass and media, a gas inlet at the bottom region of the vessel, the gas inlet positioned radially outward from the geometric center of the vessel, a barrier disposed within the vessel between the gas inlet and the geometric center of the vessel, the barrier being positioned to allow the passage of the aqueous suspension of biomass and media both under and over the barrier whereby a fluid loop is formed within the vessel around the barrier when the gas inlet is introducing gas into the vessel, and collection baffles disposed above the gas inlet configured to allow at least a portion of the media to fall toward the bottom region of the vessel without being entrained in a gas stream when the gas inlet is introducing gas into the vessel.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures.

DETAILED DESCRIPTION OF THE INVENTION

This invention will now be described with reference to several embodiments selected for illustration in the drawings. It will be appreciated that the scope and spirit of the invention are not limited to the illustrated embodiments. It will further be appreciated that the drawings are not rendered to any particular proportion or scale. Also, any dimensions referred to in the description of the illustrated embodiments are provided merely for the purpose of illustration. The invention is not limited to any particular dimensions, materials, or other details of the illustrated embodiments.

As discussed above, typical air sparging which would occur in a fluidized-bed bioreactor achieves two effects. It introduces oxygen needed for enzymatic reaction and also causes mixing and interaction within the system between system components. This intended mixing aids in oxygen mass transfer (the first effect), as well as biomass growth control through the introduction of shear forces via turbulent flow interaction between media and other parts of the system.

Figure 2:
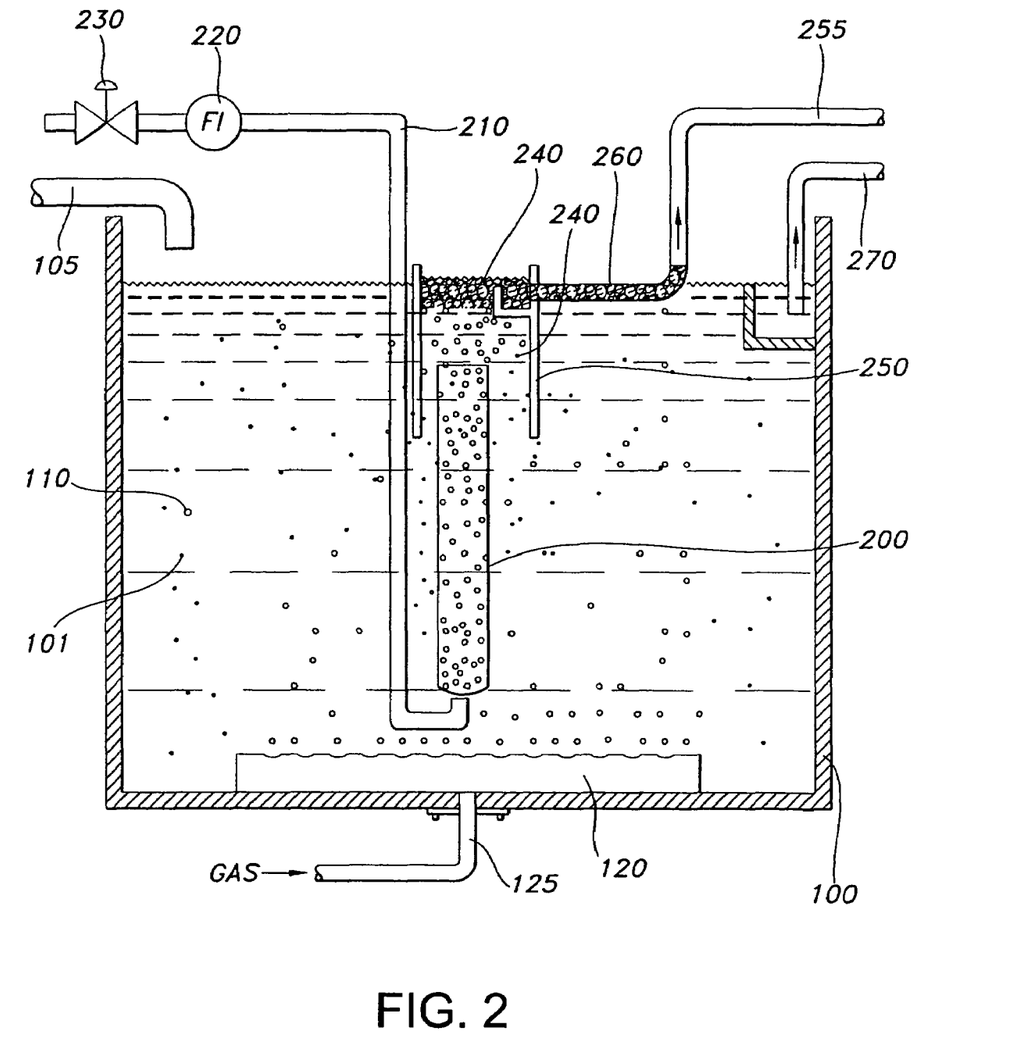
FIG. 2 schematically shows a cross-sectional view of an exemplary embodiment of a bioreactor according to aspects of the present invention with an adjustable weir and biomass removal tube.

FIG. 2 shows an exemplary embodiment of the present invention in which lift tube 200, which has an open bottom and an open top, is disposed within vessel 100. Lift tube 200 is fed gas from gas inlet line 210. Though not shown in FIG. 2, a gas source optionally feeds gas to the lift tube 200 at a location near or proximal to the inlet at the base of the lift tube 200. More specifically, according to one embodiment, the gas is delivered through a hose or tube or other conduit coupled to lift tube 200 by means of a tubing adapter fitting threaded into the side of the lift tube 200. Other arrangements are contemplated as well to provide a lift action for materials within the lift tube 200. Flow indicator 220 and valve 230 are preferably used to control gas flow into lift tube 200. Support for lift tube 200 is not shown in the schematic, partial cross-section view, but could come in any number of forms known to those skilled in the art. Also shown in FIG. 2 is treated effluent removal pipe 270 which draws treated product, namely water, from an upper peripheral, or circumferential (in the case of a round vessel), area around the top surface of the contents held in vessel 100. Optionally present in this embodiment is sparger 120 as shown in FIG. 2.

The delivery of gas into lift tube 200 causes the rise of cavities 110 within the lift tube. This causes upward flow of fluid within the lift tube as the fluid and biomass-covered media are entrained in the rising fluid. This movement, along with the movement of the cavities themselves, causes shear forces to operate on the biomass media and the biomass carried thereon and thereby causes the separation of biomass 240 from the biomass media. As the biomass 240 becomes separated from the media, it accumulates in the region just above the lift tube, as shown in FIG. 2. This accumulation is the source of controlled biomass removal in accordance with one aspect of the present invention.

More specifically, and as shown in FIG. 2, weir 250 is disposed proximal to the upper outlet of lift tube 200. Weir 250 is adjustable between a lower position and a higher position. Weir 250 is connected to pipe 255 which allows for the removal of the biomass, along with some fluid (typically water), from vessel 100. This biomass/fluid combination is shown as slurry 260 and is shown within pipe 255 being removed from vessel 100. Other means of slurry removal could be envisioned in fluid communication with adjustable weir 250, and would include manual slurry removal such as scooping of the biomass material from the weir, or suction or vacuuming of the slurry from weir 250.

Figure 8:
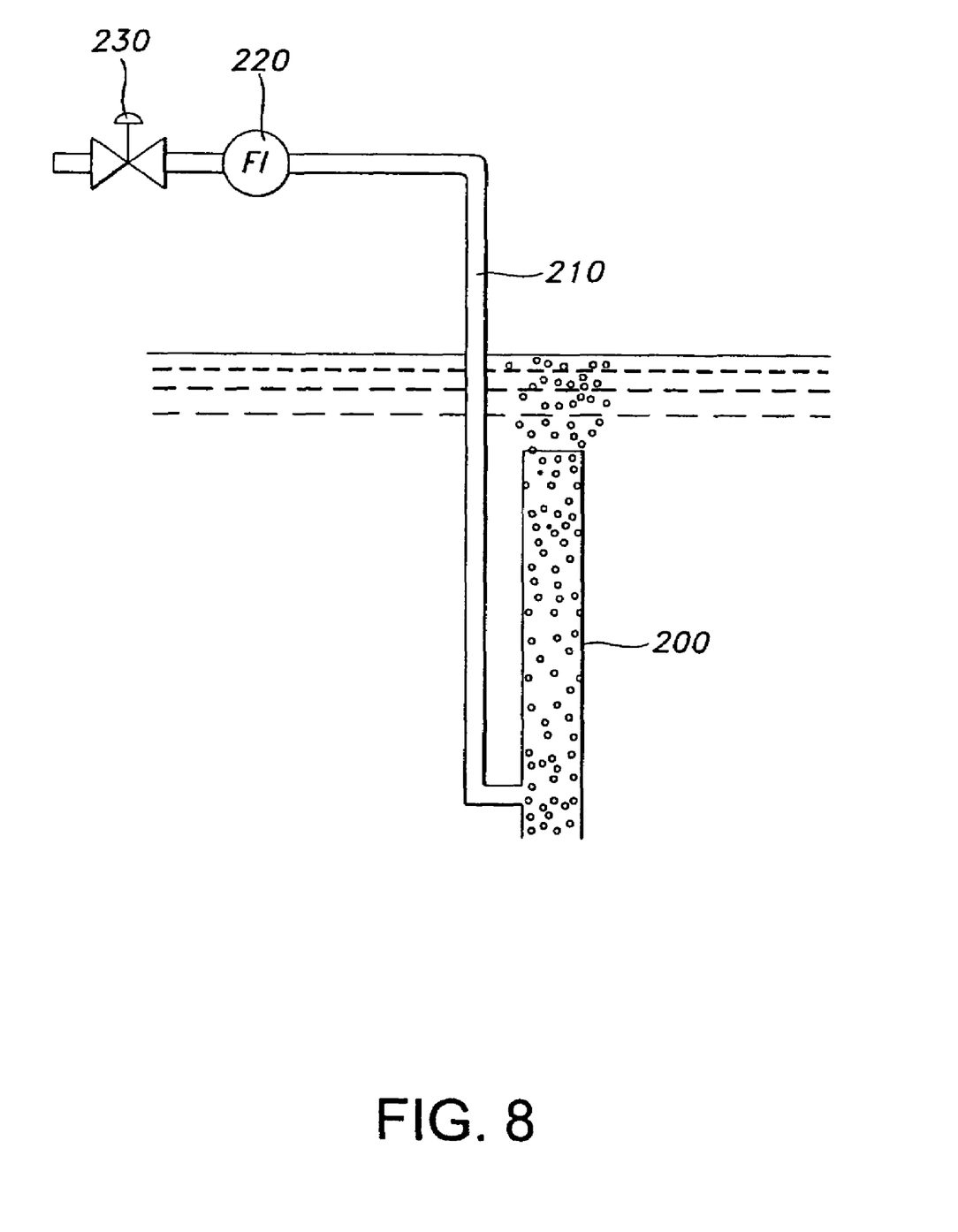
FIG. 8 schematically shows another exemplary embodiment of a lift according to aspects of the present invention.

FIG. 8 shows another exemplary embodiment of a lift according to aspects of this invention. A flow indicator 220 and a valve 230 are preferably used to control gas flow into the lift tube 200. As is shown in FIG. 8, the gas inlet line 210 through which gas is fed to the lift tube 200 can be positioned so as to have an outlet that is either positioned proximal to the inlet at the base of the lift tube 200 (as shown in FIG. 2) or can alternatively be connected to the body of the lift tube 200 (as shown in FIG. 8). In the embodiment illustrated in FIG. 8, the outlet of the gas inlet line 210 is coupled for fluid flow communication with the lift tube 200 at a location along the length of the lift tube 200.

Figure 9:
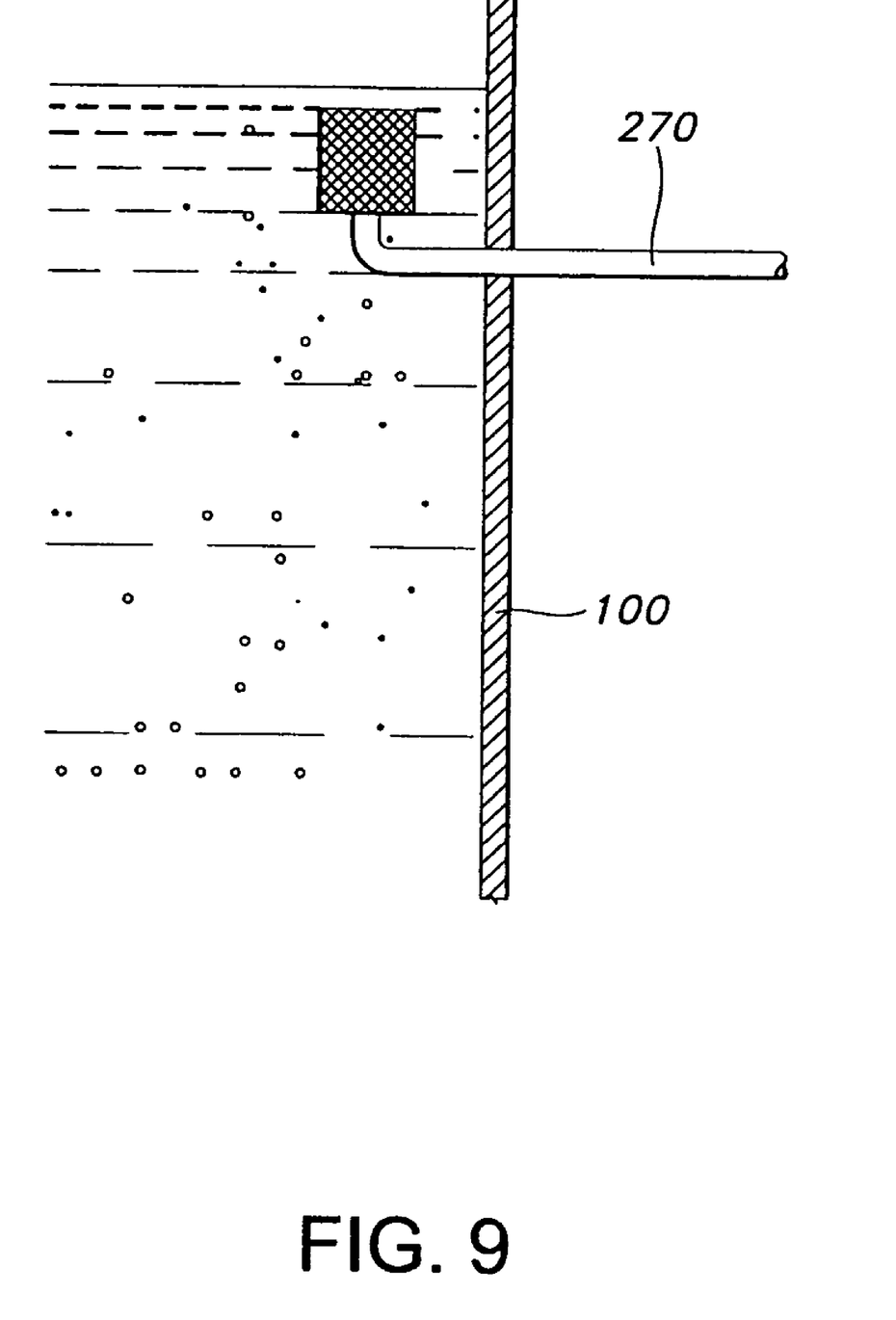
FIG. 9 schematically shows an exemplary embodiment of an effluent removal pipe according to aspects of the invention.

FIG. 9 shows another embodiment of an effluent removal pipe 270 that can be utilized according to aspects of this invention. Specifically, the treated effluent removal pipe 270 draws treated product; namely, water from an upper peripheral or circumferential area around the top surface of the contents held in the vessel 100. The effluent removal pipe 270 provides a means by which effluent can be removed from the vessel 100 during operation.

Figure 3:
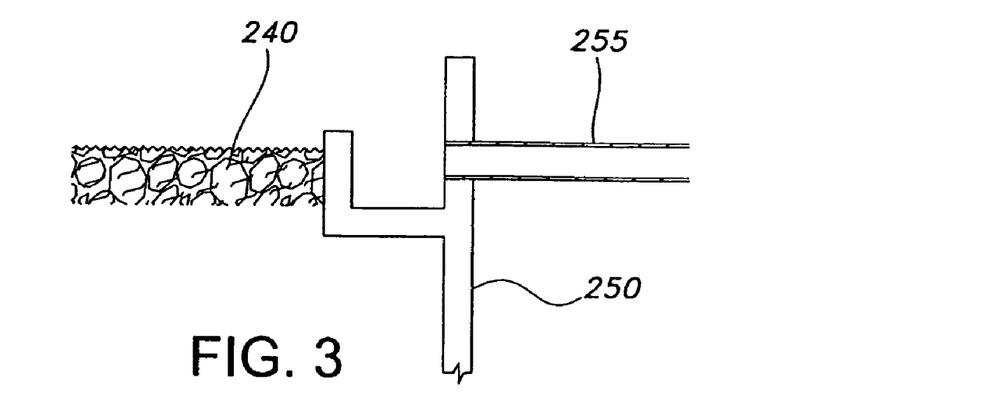
FIG. 3 schematically shows a cross-sectional view of an exemplary embodiment of a weir in an upper position in accordance with aspects of the present invention.
Figure 4:
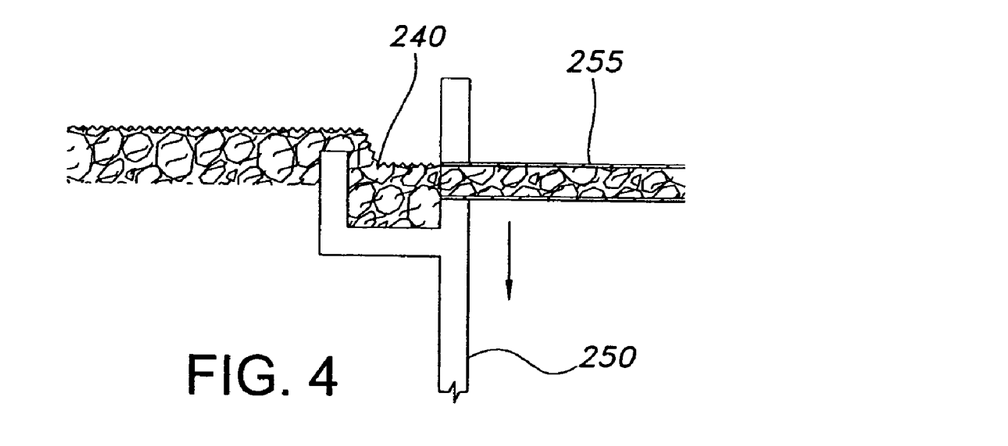
FIG. 4 schematically shows a cross-sectional view of an exemplary embodiment of a weir in an intermediate position in accordance with aspects of the present invention whereby some biomass slurry is removed.
Figure 5:
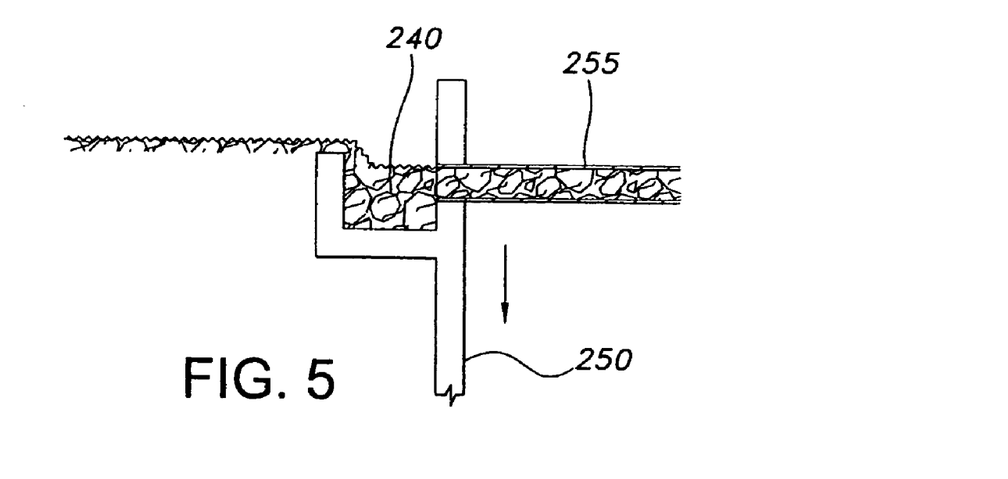
FIG. 5 schematically shows a cross-sectional view of an exemplary embodiment of a weir in a lower position in accordance with aspects of the present invention.

FIGS. 3, 4, and 5 show a schematic close-up of adjustable weir 250 in three different positions, respectively. FIG. 3 shows adjustable weir 250 in an upper, or higher, position or elevation. In this position, biomass 240 which has accumulated atop the fluid surface is not being removed because weir 250 is too high to accept the biomass into exit means (e.g. pipe) 255. FIG. 4 shows adjustable weir 250 in an intermediate position. In this position, a portion of biomass 240 is allowed to flow into weir 250 and into exit means (e.g. pipe) 255. If further removal is desired, weir 250 can be lowered even farther, as indicated by the arrow in FIG. 5. In other words, FIG. 5 shows weir 250 in a position at which point even more biomass 240 is carried out of the vessel via exit means (e.g. pipe) 255.

Another aspect of the present invention is the use of the disclosed apparatus in a novel method for achieving efficient bioreactions through careful biomass concentration control within the bioreactor. A preferred method generally comprises the steps of introducing a stream of gas into a bioreactor (e.g. near an inlet of a lift pipe) to generate sufficient shear forces to separate biomass from media, disposing a weir proximal the outlet of the lift tube in fluid communication with a point external the bioreactor, and adjusting the height or elevation of the weir to thereby control the removal of biomass from the bioreactor.

Preferably, the method operates by passing air into the bioreactor, although oxygen enriched air or even pure oxygen could be used. In a typical application of the present method, the bioreactor is used to treat waste water, whereby a stream of contaminated water or sewage is introduced into the vessel and, after sufficient enzymatic activity is allowed to occur, a purified water stream from the bioreactor is removed via effluent removal pipe 270.

Figure 6:
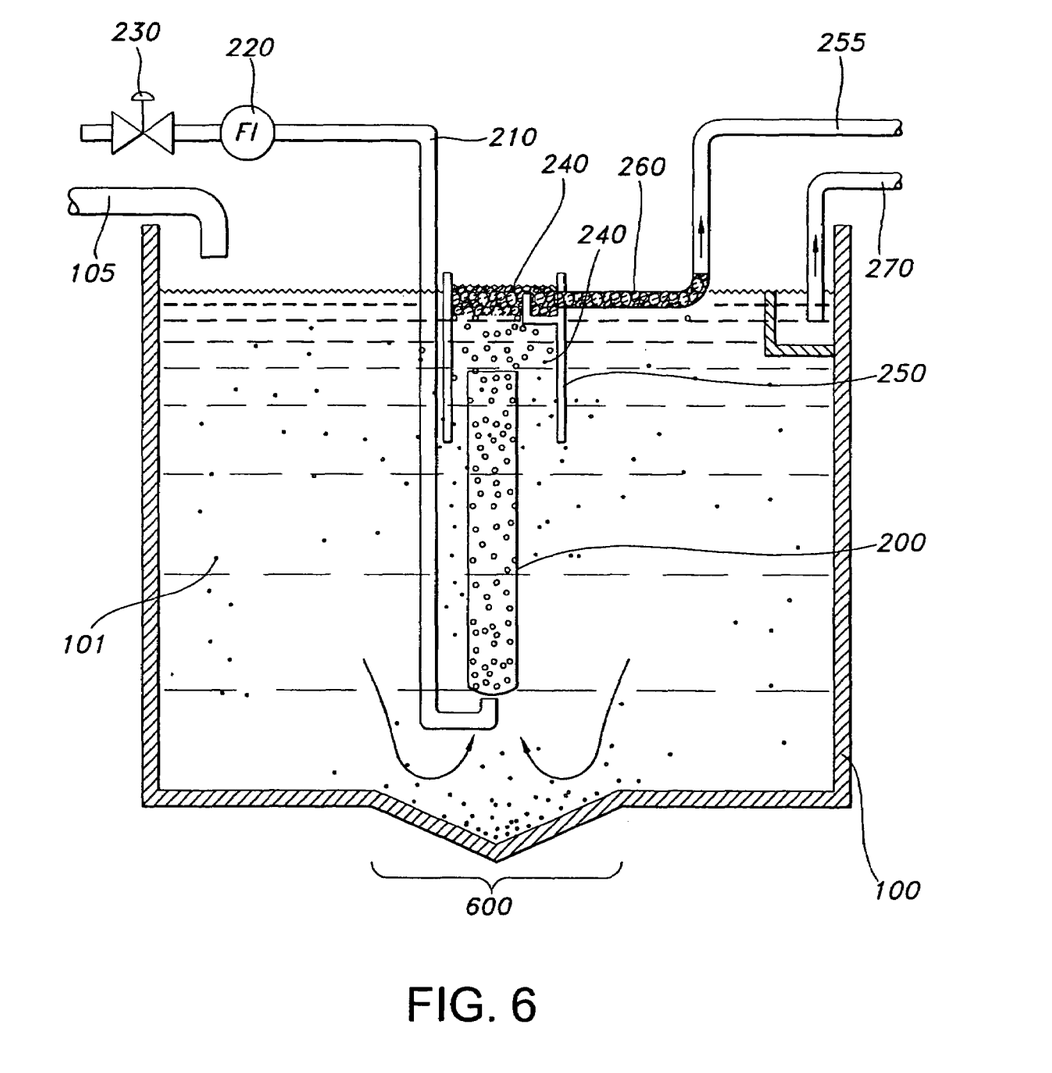
FIG. 6 shows a partial cross-sectional view of another exemplary embodiment of the present invention wherein a reactor has a quiescent zone disposed proximal to a lift tube inlet.
Figure 7:
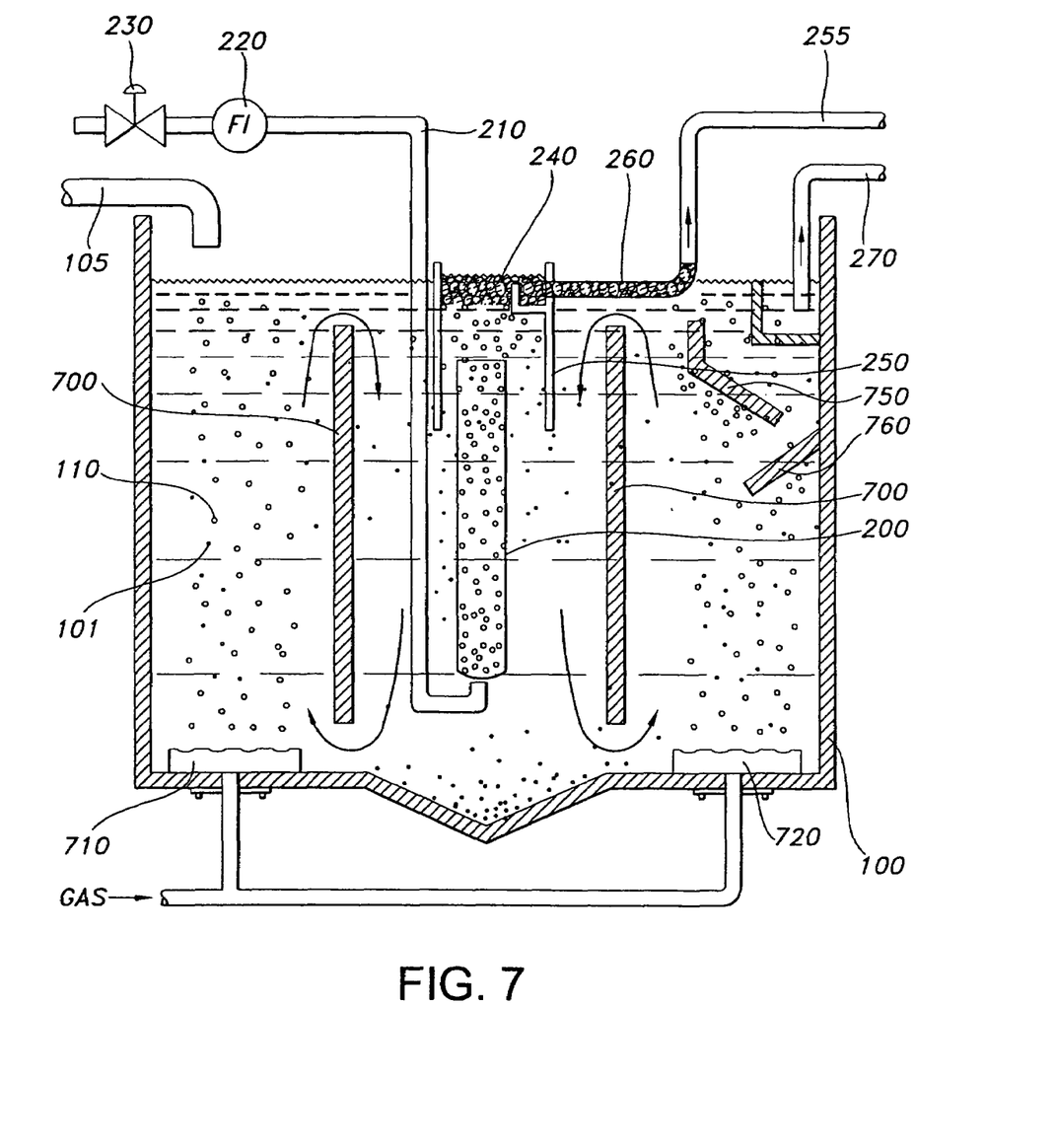
FIG. 7 shows a partial cross-sectional view of yet another exemplary embodiment of the present invention having a barrier and gas inlet to produce a fluid-flow loop, and collection baffles, all in accordance with aspects of the present invention.

Other exemplary features of an embodiment of the invention are shown in FIGS. 6 and 7. FIG. 6 shows vessel 100 without sparger 120 but with quiescent zone 600 formed into the bottom of vessel 100. Quiescent zone 600 allows for the settlement of both biomass and media as it falls from the top regions of vessel 100. Quiescent zone 600 in this embodiment is a concave area or region disposed within the bottom of vessel 100. Preferably quiescent zone 600 has sloping sides, as shown in FIG. 6, but could be an indented area or region with sides perpendicular to, or at other angles or curvatures with respect to, the bottom of vessel 100.

Because lift tube 200, in conjunction with its gas inlet line 210, causes an upward flow of fluid and resultant upward movement of media and biomass which is entrained in the upward moving fluid, a fluid flow, or current, is developed within the system as shown by the arrows in FIG. 6. As biomass and media is separated within lift tube 200 as during its ascent, media exits the top of lift tube 200 and falls toward the bottom of vessel 100. Much of the media is collected in quiescent zone 600. When it is covered again in biomass, and thereby has its density decreased slightly as its volume grows, it is pulled upward as entrained matter into lift tube 200 where it is again separated and the biomass is removed in accordance with the operation of weir 250 as noted above. Of course, other means of biomass removal could be used in conjunction with quiescent zone 600 and lift tube 200 as noted above in the discussion of adjustable weir 250.

Aiding in the settlement of media in quiescent zone 600 are lift loops shown by arrows indicating fluid flow in FIG. 7. These lift loops are created by the use of barrier(s) 700 in conjunction with at least one second gas inlet, such as gas inlets 710 and 720. Barrier(s) 700 is disposed radially within the vessel between the gas inlets and the geometric center of the vessel. In the case where vessel 100 is round, the barrier is optionally a concentric barrier extending around the central axis (or geometric center whether or not the vessel is round)

of vessel 100 between lift tube 200 and the gas inlet(s). In the case where vessel 100 is, say, square, barrier 700 is also optionally square and would have dimensions such that it fits between the lift tube and air inlets.

The idea is that, no matter the shape or configuration of the vessel and barrier, the barrier according to this embodiment is disposed radially between the lift tube and gas inlets so as to provide for a fluid flow loop whereby fluid flows upward outside of the barrier and downward inside the barrier, as shown by the arrows indicating flow in FIG. 7. The lift loops shown are generated by the upward movement of fluid (and entrained biomass and media) in the area between the walls of vessel 100 and barrier(s) 700. As this fluid moves upward, it is replaced by fluid flowing downward in the area between barrier(s) 700 and lift tube 200.

Also shown in FIG. 7 is an embodiment of the invention having collection baffles 750 and 760. Collection baffles 750 and 760 are shown disposed above gas inlet 720 to prevent gas cavities from gas inlet 720 from carrying media and/or biomass into the area where effluent take-off occurs through treated effluent removal pipe 270. As can be appreciated through a consideration of the configuration shown in FIG. 7, cavities from gas inlet 720 are deflected away from the inlet of treated effluent removal pipe 270 by baffles 750 and 760 as they ascend, but media and/or biomass is allowed to descend around baffles 750 and 760 and return toward the bottom of vessel 100. Although only shown above gas inlet 720 (because the view is a partial cross-sectional view), these baffles could extend around vessel 100 continuously or wherever a gas inlet(s) is disposed to achieve this above-described function. Further details of exemplary gas inlets are provided in application Ser. No. 10/682,624, filed Oct. 9, 2003, which is incorporated by reference herein.

Included as a part of the present invention is the use of the various apparatus in novel methods for achieving efficient bioreactions through careful biomass concentration control within the bioreactor. In addition to the method described above, another preferred method generally comprises the steps of introducing a stream of gas into a bioreactor near an inlet of a lift pipe to generate sufficient shear forces to separate biomass from the media, and generating at least one flow loop within the bioreactor to allow for media settlement within a quiescent zone disposed near the bottom center of the bioreactor, whereby the quiescent zone feeds biomass covered media to the bottom of the lift tube. A preferred means of generating the flow loop is the use of a barrier and a gas inlet (separate from the lift tube gas inlet) to create a lift loop for upward fluid flow between the barrier and vessel wall.

Also included is a method of generating a cleaned effluent stream comprising the steps of introducing a stream of gas into a bioreactor below at least one collection baffle, and removing a cleaned effluent stream above the collection baffles, whereby entrained media and/or biomass is prevented from entering the area of the bioreactor where effluent product is removed.

Still other methods of using the various disclosed embodiments, including specific combinations thereof, could be envisioned by one skilled in the art with the benefit of the foregoing. These and other methods are considered a part of the present invention.

Figure 10:
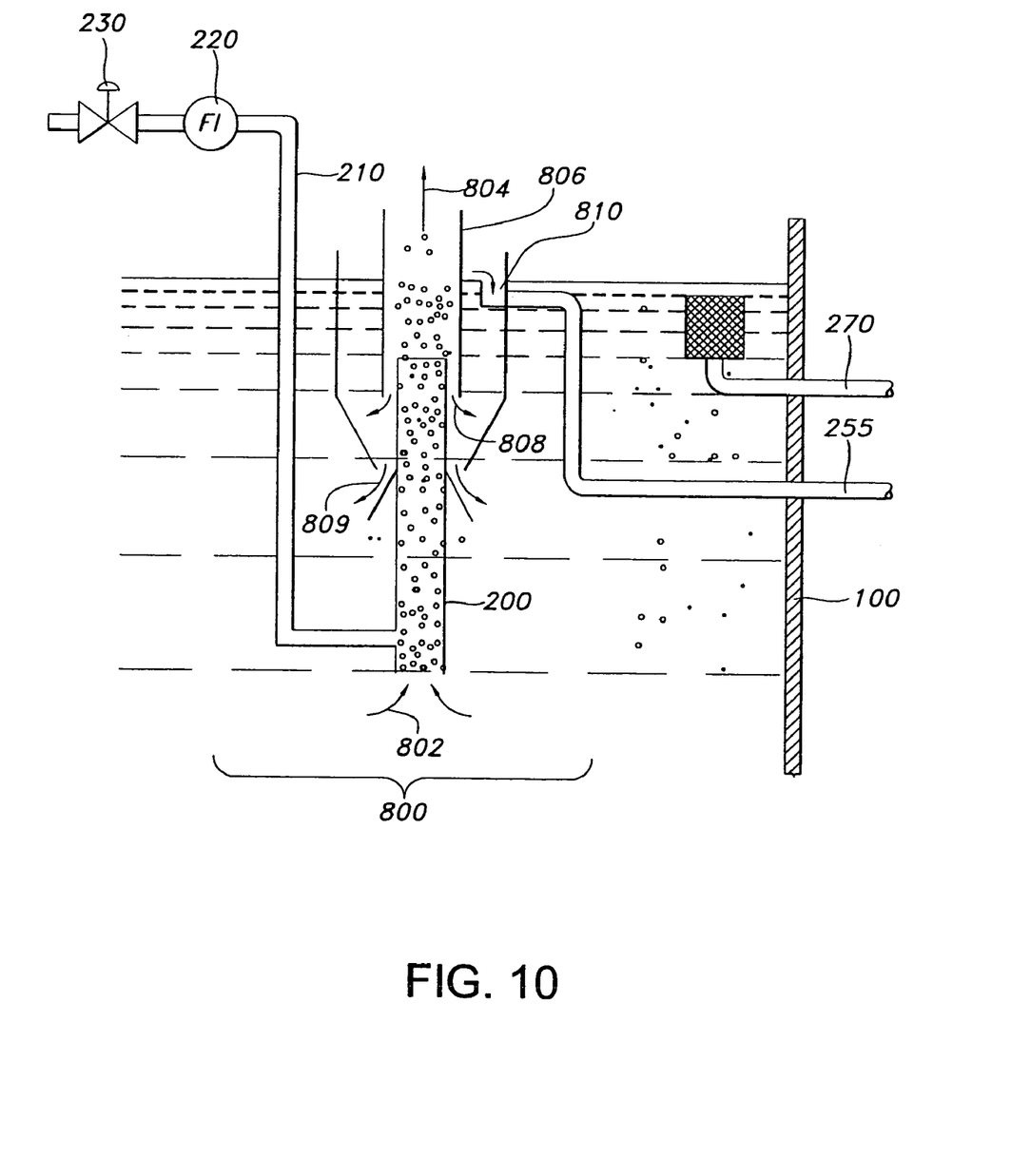
FIG. 10 schematically shows another exemplary embodiment of a bioreactor according to aspects of the present invention.

FIG. 10 shows another exemplary embodiment of a bioreactor in schematic form. The bioreactor of FIG. 10 includes a separator body 800 including a lift. More specifically, the separator body 800 is similar to that illustrated in FIG. 8 in that the lift tube 200 is provided with inlet air or gas by means of a passage way 210 that is connected to the lift tube 200 to introduce gas or air. The assembly 800 differs from that shown in connection with prior embodiments in that the separator includes an inlet 802 at its base for the inlet of media coated with biomass into the lift pipe, an air release baffle 806 through which air 804 is released from the separator and media and biomass 808 flow downwardly between the lift pipe 200 and the air release baffle 806, a clean media return 809 through which clean media returns to the interior of the vessel, and a weir for biomass suspension 810 for delivering biomass to an outlet tube 255 for removal from the vessel 100.

Although preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A bioreactor comprising:
   a vessel configured to contain an aqueous suspension of biomass and media;
   a lift tube disposed within the vessel, the lift tube having an inlet disposed at a bottom region of the vessel and an outlet disposed at a top region of the vessel;
   a gas inlet positioned to feed gas into the lift tube, said gas inlet configured to introduce a stream of gas to promote separation of said biomass from said media in said lift tube;
   an adjustable weir disposed proximal to the outlet of the lift tube, the weir being adjustable to an elevation below a fluid surface in said bioreactor and between a lower elevation and a higher elevation; and
   means for removing biomass from said weir, said biomass removing means being in fluid communication with said weir;
   wherein the elevation of the weir is adjustable to control the removal of biomass from the vessel.

2. The bioreactor of claim 1 wherein said biomass removal means is a pipe.

3. The bioreactor of claim 1 wherein the gas inlet comprises a fine bubble aerator.

4. The bioreactor of claim 1 further comprising a source of air wherein the gas introduced from said gas inlet is air from said source of air.

5. The bioreactor of claim 1 further comprising a source of oxygen wherein the gas introduced from said gas inlet is oxygen from said source of oxygen.

6. The bioreactor of claim 1 wherein the vessel is a waste water treatment vessel.

7. The bioreactor of claim 1 wherein the lift tube is oriented substantially vertically within the vessel.

8. A method for controlling the removal of biomass from a bioreactor, the method comprising the steps of:
   introducing a stream of gas into a lift tube proximal an inlet of the lift tube at a bottom region of the bioreactor to generate sufficient shear forces to separate biomass from media in the bioreactor;
   delivering biomass from the lift tube to a weir proximal an outlet of the lift tube for removal from the bioreactor; and
   adjusting the elevation of the weir to an elevation below a fluid surface in said bioreactor to thereby control the removal of biomass from the bioreactor.

9. The method of claim 8 wherein said adjusting step comprises raising the weir to decrease the amount of biomass removed from the bioreactor.

10. The method of claim 8 wherein said adjusting step comprises lowering the weir to increase the amount of biomass removed from the bioreactor.

11. The method of claim 8 wherein said introducing step is performed using an air sparger.

12. The method of claim 11 wherein said introducing step comprises passing the gas through a fine bubble aerator.

13. The method of claim 8 wherein said introducing step comprises introducing air.

14. The method of claim 8 wherein said introducing step comprises introducing oxygen.

15. The method of claim 8 further comprising the step of treating waste water in the bioreactor.

16. The method of claim 8 further comprising the step of adding a contaminated waste water stream into the vessel before said introducing step.

17. The method of claim 16 further comprising the step of removing a treated water stream from the bioreactor.

* * * * *